(12) United States Patent
Kamakura et al.

(10) Patent No.: US 9,168,235 B2
(45) Date of Patent: Oct. 27, 2015

(54) AQUEOUS PATCHES CONTAINING DICLOFENAC SODIUM

(75) Inventors: Takashi Kamakura, Higashikagawa (JP); Kazuha Tani, Higashikagawa (JP); Yuichiro Mabuchi, Higashikagawa (JP); Kazuhito Okada, Higashikagawa (JP)

(73) Assignee: Teikoku Seiyaku Co., Ltd., Kagawa (JP)

( * ) Notice: Subject to any disclaimer, the term of this patent is extended or adjusted under 35 U.S.C. 154(b) by 3 days.

(21) Appl. No.: 13/502,558

(22) PCT Filed: Oct. 19, 2010

(86) PCT No.: PCT/JP2010/068311
§ 371 (c)(1),
(2), (4) Date: Apr. 18, 2012

(87) PCT Pub. No.: WO2011/049058
PCT Pub. Date: Apr. 28, 2011

(65) Prior Publication Data
US 2012/0207814 A1     Aug. 16, 2012

(30) Foreign Application Priority Data
Oct. 23, 2009   (JP) ................................. 2009-244518

(51) Int. Cl.
| | | |
|---|---|---|
| *A61K 8/03* | (2006.01) | |
| *A61K 31/196* | (2006.01) | |
| *A61K 9/00* | (2006.01) | |
| *A61K 9/70* | (2006.01) | |
| *A61K 47/02* | (2006.01) | |
| *A61K 47/10* | (2006.01) | |
| *A61K 47/14* | (2006.01) | |
| *A61K 47/32* | (2006.01) | |
| *A61K 47/38* | (2006.01) | |

(52) U.S. Cl.
CPC ............ *A61K 31/196* (2013.01); *A61K 9/0012* (2013.01); *A61K 9/7084* (2013.01); *A61K 47/02* (2013.01); *A61K 47/10* (2013.01); *A61K 47/14* (2013.01); *A61K 47/32* (2013.01); *A61K 47/38* (2013.01)

(58) Field of Classification Search
CPC . A61K 9/0002; A61K 9/0012; A61K 9/7023; A61L 26/009; A61L 26/0095
USPC .......................................................... 424/449
See application file for complete search history.

(56) References Cited

U.S. PATENT DOCUMENTS

| | | | | |
|---|---|---|---|---|
| 4,952,560 | A | * | 8/1990 | Kigasawa et al. .......... 514/21.92 |
| 5,208,035 | A | * | 5/1993 | Okuyama et al. .............. 424/446 |
| 2002/0005028 | A1 | * | 1/2002 | Shudo ............................. 53/424 |
| 2004/0146548 | A1 | | 7/2004 | Takada et al. |
| 2007/0280980 | A1 | * | 12/2007 | Hashimoto et al. ........... 424/402 |
| 2008/0113010 | A1 | | 5/2008 | Yama et al. |
| 2010/0022614 | A1 | | 1/2010 | Kawamura et al. |

FOREIGN PATENT DOCUMENTS

| | | |
|---|---|---|
| CN | 1511027 A | 7/2004 |
| CN | 101052384 A | 10/2007 |
| CN | 101553213 A | 10/2009 |
| JP | 04-217925 | 8/1992 |
| JP | 05-032544 | 2/1993 |
| JP | 06-219940 | 8/1994 |
| JP | 07-089853 | 4/1995 |
| JP | 11-222443 | 8/1999 |
| JP | 2004-43512 | 2/2004 |
| WO | 2004/071499 | 8/2004 |
| WO | 2005/102306 | 11/2005 |

OTHER PUBLICATIONS

International Preliminary Report on Patentability issued May 15, 2012 in International Application No. PCT/JP2010/068311, of which the present application is the national stage.
English translation of Office Action issued Dec. 17, 2012 in corresponding Chinese Application No. 201080049058.5.
Supplementary European Search Report issued Mar. 11, 2013 in corresponding European Application No. 10 82 4907.

\* cited by examiner

*Primary Examiner* — Michael G Hartley
*Assistant Examiner* — Micah-Paul Young
(74) *Attorney, Agent, or Firm* — Wenderoth, Lind & Ponack, L.L.P.

(57) ABSTRACT

An aqueous patch containing diclofenac sodium, wherein the patch contains a homogeneous mixed solution of diclofenac sodium, wherein the solution is obtained by mixing crotamiton, diclofenac sodium and water in the mixture ratio of crotamiton/diclofenac sodium of 8.0 or less and the mixture ratio of (water+crotamiton)/diclofenac sodium of 3.0-20.0.

6 Claims, 1 Drawing Sheet

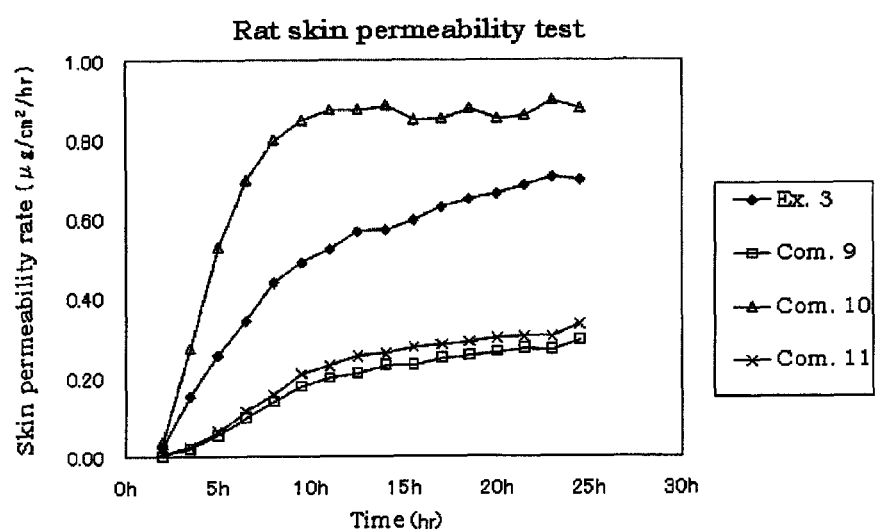

AQUEOUS PATCHES CONTAINING DICLOFENAC SODIUM

TECHNICAL FIELD

The present invention relates to an aqueous patch containing diclofenac sodium as an active ingredient for transdermal absorption. More specifically, the present invention relates to an aqueous patch containing diclofenac sodium for transdermal absorption which shows an excellent dissolution stability of diclofenac sodium, a high initial release rate of the drug and a sustained release of the drug.

BACKGROUND ART

Recently, many non-steroidal anti-inflammatory analgesics for transdermal absorption have been formulated and widely used for various inflammatory diseases such as chronic rheumatism, osteoarthritis, spondylosis deformans, and low back pain. Especially, diclofenac sodium has an excellent anti-inflammatory analgesic action, and therefore, is widely used as an oral agent or a suppository in clinical scenes. However, diclofenac sodium is also known to cause various side effects such as gastrointestinal disease.

In order to alleviate these side effects, an external preparation for transdermal absorption of diclofenac sodium has been investigated.

Especially, an external patch enables an efficient and continuous treatment because it can control a drug dosage and directly transfer a drug to the affected area just below the patch. However, diclofenac sodium has a very low solubility in water or an oily ingredient. Therefore, it is difficult to prepare a patch in which diclofenac sodium is completely dissolved, and even if such patch can be prepared by the addition of an excessive amount of an agent such as a diclofenac sodium solubilizer, it is difficult to preserve such patch with diclofenac sodium remaining in the dissolved state without a crystal precipitation in the patch for a long time. Also, when an oily ingredient which can highly dissolve diclofenac sodium is contained in an aqueous patch at a high concentration, the compatibility with other ingredients becomes worse, a phase separation readily occurs, and a stable storage for a long time becomes impossible. In addition, because the transdermal absorbability of diclofenac sodium is generally low, various investigations or efforts have been performed until now to solve these problems. However, a formulation which can solve the above problems has not been obtained so far.

For example, the following Patent Document 1 proposes a patch with an enhanced transdermal absorbability of diclofenac sodium prepared by adding crotamiton and a weak fatty acid to diclofenac sodium to convert the drug to a free acid. However, the stability of diclofenac sodium may be lowered by converting diclofenac sodium to the free acid, and further, the transdermal absorbability of the drug is not sufficiently high.

The following Patent Document 2 proposes a patch which has an excellent transdermal absorption efficiency of diclofenac sodium and a small chronological change consisting of two layers, i.e., an agent layer containing diclofenac sodium and a base layer not containing diclofenac sodium. However, because the preparation of this patch requires a process for pasting the agent layer and the base layer after they are separately prepared and spread, there are problems in complicated process management, economic efficiency, etc.

The following Patent Document 3 proposes an aqueous patch containing diclofenac sodium, an absorption enhancer consisting of 1-menthol and propylene glycol, and a hydrophilic base comprising a water-soluble polymer as the main ingredient. However, the solubility of diclofenac sodium in the patch is low and there is a fear of crystallization of the drug during a long storage, and further, the transdermal absorbability of the drug is not sufficiently high.

The following Patent Document 4 proposes the addition of 1-menthol and pyrrolidones (at least one of pyrrolidone or derivatives thereof) as transdermal absorption enhancers of diclofenac sodium. However, the solubility of diclofenac sodium in the aqueous patch is low and there is a fear of crystallization of the drug during a long storage, and further, the transdermal absorbability of the drug is not sufficiently high.

Patent Document 1: JP 07-089853 A
Patent Document 2: WO 2004/071499
Patent Document 3: JP 05-032544 A
Patent Document 4: JP 11-222443 A

DISCLOSURE OF INVENTION

Problems to be Solved by the Invention

The object of the present invention is to provide an aqueous patch which shows an excellent dissolution stability and an excellent transdermal absorbability of diclofenac sodium. In other words, the object of the present invention is to provide an aqueous patch which does not cause a crystal precipitation of the drug in a plaster even after a long time storage, and shows an excellent initial release rate of the drug and a sustained release of the drug.

Means for Solving the Problems

The present inventors have studied earnestly in order to solve the preceding problems, and as a result, surprisingly found that a mixed solution consisting of crotamiton, water, and diclofenac sodium (which can hardly be dissolved in either crotamiton or water alone) wherein the mixture ratio of crotamiton/diclofenac sodium is 8.0 or less and the mixture ratio of (water+crotamiton)/diclofenac sodium is in the range of 3.0-20.0 unexpectedly enables enhancing the solubility of diclofenac sodium and preparing a homogeneous diclofenac sodium-completely dissolved solution (hereinafter referred to as a diclofenac sodium-principal drug solution of the present invention).

Accordingly, by using this mixed solution, an aqueous patch which does not cause crystallization in a plaster, and shows an excellent dissolution stability of diclofenac sodium, a high initial release rate of the drug, and a sustained release of the drug can be obtained.

Effect of the Invention

In other words, the present invention provides an aqueous patch which shows an excellent dissolution stability of diclofenac sodium, a high initial release rate of the drug, and a sustained release of the drug, by using a homogeneous mixed solution (diclofenac sodium-principal drug solution of the present invention) obtained by mixing crotamiton, diclofenac sodium and water in the mixture ratio of crotamiton/diclofenac sodium of 8.0 or less and the mixture ratio of (water+crotamiton)/diclofenac sodium of 3.0-20.0.

BRIEF DESCRIPTION OF DRAWINGS

FIG. 1 is a graph which shows each relation between a permeability rate of diclofenac sodium which permeated a skin of a hairless rat and time described in the Experimental Example 3.

BEST MODE FOR CARRYING OUT THE INVENTION

Hereinafter, more detailed descriptions about the preferred embodiments of the aqueous patch containing diclofenac sodium of the present invention are provided.

The amount of diclofenac sodium, which is an active ingredient of the aqueous patch of the present invention, in the plaster is 0.1-5% by weight, preferably 0.5-2.5% by weight. The amount less than 0.1% is not preferred because such amount causes an insufficient pharmacological effect. On the other hand, when the amount is more than 5% by weight, such amount readily causes a crystal precipitation of diclofenac sodium and a worse physical property of the formulation.

The amount of crotamiton in the plaster is 1.5-5% by weight, preferably 2-4% by weight. When the amount is less than 1.5% by weight, the homogeneous mixed solution of diclofenac sodium/water/crotamiton can not be prepared, the solubility of diclofenac sodium in the plaster decreases, and the initial transdermal absorbability becomes insufficient. On the other hand, when the amount is more than 5% by weight, the compatibility with other ingredients becomes worse, crotamiton bleeds out to the plaster surface, diclofenac sodium is released, the adhesive power of the formulation decreases, and excellent physical properties of the formulation becomes difficult to be maintained for a long time.

In the present invention, water is an essential ingredient for preparing the diclofenac sodium-principal drug solution, and also a necessary ingredient as a solubilizer of ingredients of the plaster of the aqueous patch such as a water-soluble polymer. The amount of water for preparing the diclofenac sodium-principal drug solution of the present invention is 0.5-20%, preferably 1-10% per plaster weight. When the amount is outside this range, the homogeneous diclofenac sodium-principal drug solution can not be prepared. Also, the amount of water for dissolving ingredients of the plaster (which comprises the amounts of water already contained in the ingredients, such as the amount of water contained in 20% polyacrylic acid aqueous solution) is determined in view of the composition of the plaster and the balance with the amount of water for preparing diclofenac sodium, and is 20-50% by weight, preferably 30-45% by weight per plaster weight.

The total amount of water per plaster is 20-70%, preferably 30-60% by weight. When the amount is more than 70% by weight, the viscosity of the plaster decreases, and as a result, the shape retention ability of the plaster decreases and the plaster becomes sticky. Furthermore, such a high amount is not preferable because it causes a significantly decreased adhesive power of the formulation, and as a result, the formulation can not strongly adhere to an application site. Meanwhile, when the amount is less than 20% by weight, the viscosity of the plaster becomes too high and the efficiency in the preparation becomes worse. In addition, such a low amount is not preferable because it causes a too strong adhesive power of the formulation, and therefore, when releasing the formulation from a skin, a skin irritation such as a pain occurs.

The diclofenac sodium-principal drug solution of the present invention, which is the feature of the present invention, contains each ingredient in the composition ratio of crotamiton/diclofenac sodium of 8.0 or less and (water+crotamiton)/diclofenac sodium in the range of 3.0-20.0. When the ratio of the each ingredient is outside this composition ratio, the homogeneous diclofenac sodium-principal drug solution can not be prepared.

The ingredients of the plaster constituting the aqueous patch may be those which are used in the preparation of a common aqueous patch, and for example, an ingredient such as, but is not limited to, a water-soluble polymer, a humectant, an excipient, a stabilizing agent, a cross-linking agent, an antioxidant, a cooling agent, or a calefacient, etc. can be contained in the plaster.

As the water-soluble polymer, for example, gelatin, hydrolyzed gelatin, polyacrylic acid, sodium polyacrylate, partially neutralized polyacrylic acid, starch polyacrylate, polyvinyl alcohol, polyvinylpyrrolidone, hydroxypropylcellulose, hydroxypropylmethylcellulose, hydroxyethylcellulose, methylcellulose, carmellose sodium, carboxyvinyl polymer, methoxyethylene-maleic anhydride copolymer, N-vinylacetamide copolymer, xanthane gum, or gum arabic, etc. can be used singly or in a combination thereof. Especially, a combination of polyacrylic acid, partially neutralized polyacrylic acid, and carmellose sodium is preferred.

As the humectant, for example, concentrated glycerin, D-sorbitol solution, 1,3-butylene glycol, dipropylene glycol, or polyethylene glycol, etc. can be used singly or in a combination thereof.

As the excipient, for example, kaolin, titanium oxide, anhydrous silicic acid, zinc oxide, or bentonite, etc. can be used singly or in a combination thereof.

As the stabilizing agent, for example, edetate, tartaric acid, citric acid, sodium bisulfite, or diisopropanolamine, etc. can be used singly or in a combination thereof.

As the cross-linking agent, for example, a polyvalent metal compound such as dried aluminum hydroxide gel, synthetic aluminum silicate, dihydroxyaluminum aminoacetate, synthetic hydrotalcite, magnesium aluminometasilicate, or magnesium aluminosilicate, etc. can be used singly or in a combination thereof.

As the antioxidant, for example, tocopherol acetate, ascorbic acid, butylhydroxytoluene, or tocopherol, etc. can be used singly or in a combination thereof.

As the cooling agent, mentha oil, dl-camphor, or d-borneol, etc. may be used singly or in a combination thereof.

As the calefacient, a Capsicum-derived material such as powdered Capsicum, Capsicum extract, or Capsicum tincture, etc., capsaicin or a capsaicin analog such as dihydroxy capsaicin or capsinoid, etc., nonylic acid vanillylamide, or benzyl nicotinate may be used singly or in a combination thereof.

In addition, as an ingredient of the plaster constituting the aqueous patch of the present invention, if necessary, a preservative, a plasticizer, an emulsifying agent, or a surfactant, etc. can be contained.

Furthermore, the pH of the plaster composition of the present invention is preferably in the range of pH 3.5-7.0, more preferably in the range of pH 4.0-6.0 in view of the skin irritation.

The process for preparing the aqueous patch containing diclofenac sodium of the present invention is not limited to a specific process and may be a known process, except in that the principal drug, i.e., diclofenac sodium, is prepared into the preceding diclofenac sodium-principal drug solution of the present invention, and then the solution is added to the other plaster composition of the aqueous patch. For example, the aqueous patch containing diclofenac sodium can be formed by spreading the plaster composition having the above-exemplified constitution on a support, and if necessary, coating the surface of the plaster composition with a plastic film.

As the plastic film for coating the surface of the plaster composition, a monolayer or a composite film of polyethylene, polypropylene, polyester, or polyvinyl chloride can be used, and further, the surface of the film may be subject to a silicon treatment, a corona discharge treatment, a roughening treatment, or a plasma treatment, etc.

As the support, a porous material, a foam, a woven fabric, or a non-woven fabric of polyethylene, polypropylene, polyvinyl chloride, polyester, nylon, or polyurethane, etc., and additionally, a laminate of a plastic film or sheet with a porous material, a foam, a woven fabric, or a non-woven fabric, etc. can be used.

EXAMPLE

The present invention is more specifically illustrated by the following Examples and Experimental Examples, but the present invention is not limited to them. Also, in Examples, the indication with "S" such as "Example 1S" indicates the diclofenac sodium-principal drug solution of the present invention used in an experiment etc. and the indication without "S" indicates the patch as the final formulation of the present invention containing each of the diclofenac sodium-principal drug solution of the present invention.

Experimental Example 1

<Drug Solubility Test>

The solubility of diclofenac sodium in each of the diclofenac sodium-principal drug solution obtained by mixing diclofenac sodium/crotamiton/purified water in a predefined ratio was visually observed (Examples 1(S)-11(S) and Comparative Examples 1(S)-12(S)). The results are shown in Table 1-1 and Table 1-2 respectively.

TABLE 1-1

Solubility of diclofenac sodium in the diclofenac sodium-principal drug solution of the present invention (Examples (Ex.))

| Ingredient | Ex. 1S | Ex. 2S | Ex. 3S | Ex. 4S | Ex. 5S | Ex. 6S | Ex. 7S | Ex. 8S | Ex. 9S | Ex. 10S | Ex. 11S |
|---|---|---|---|---|---|---|---|---|---|---|---|
| Diclofenac sodium | 1.0 | 1.0 | 1.0 | 1.0 | 1.0 | 1.0 | 1.0 | 1.0 | 0.5 | 2.0 | 3.0 |
| Crotamiton | 2.0 | 2.0 | 4.0 | 2.0 | 2.0 | 5.0 | 1.0 | 5.0 | 2.0 | 4.0 | 4.0 |
| Purified water | 1.0 | 6.0 | 2.0 | 2.0 | 18.0 | 1.0 | 15.0 | 2.0 | 1.0 | 6.0 | 6.0 |
| (Water + Crotamiton)/Diclofenac sodium | 3.0 | 8.0 | 6.0 | 4.0 | 20.0 | 6.0 | 16.0 | 7.0 | 6.0 | 5.0 | 3.3 |
| Crotamiton/Diclofenac sodium | 2.0 | 2.0 | 4.0 | 2.0 | 2.0 | 5.0 | 1.0 | 5.0 | 4.0 | 2.0 | 1.3 |
| Solubility | ○ | ○ | ○ | ○ | ○ | ○ | ○ | ○ | ○ | ○ | ○ |

○: Completely dissolved

TABLE 1-2

Solubility of diclofenac sodium in the diclofenac sodium-principal drug solution (Comparative Examples (Com.))

| Ingredient | Com. 1S | Com. 2S | Com. 3S | Com. 4S | Com. 5S | Com. 6S | Com. 7S | Com. 8S | Com. 9S | Com. 10S | Com. 11S | Com. 12S |
|---|---|---|---|---|---|---|---|---|---|---|---|---|
| Diclofenac sodium | 1.0 | 1.0 | 1.0 | 1.0 | 1.0 | 1.0 | 2.0 | 3.0 | 1.0 | 1.0 | 1.0 | 1.0 |
| Crotamiton | 2.0 | — | 10.0 | 2.0 | 5.0 | 4.0 | 2.0 | 2.0 | — | 0.5 | — | 2.0 |
| Purified water | — | 3.0 | 2.0 | 38.0 | 20.0 | 40.0 | 1.0 | 3.0 | — | — | — | — |
| Propylene glycol | — | — | — | — | — | — | — | — | 3.0 | — | — | — |
| N-Methyl-2-pyrrolidone | — | — | — | — | — | — | — | — | — | — | 2.0 | — |
| Lauromacrogol (Polyoxyethylene laurylether) | — | — | — | — | — | — | — | — | — | 2.0 | — | — |
| Diisopropyl adipate | — | — | — | — | — | — | — | — | — | 1.0 | — | — |
| Oleic acid | — | — | — | — | — | — | — | — | — | — | — | 2.0 |
| (Water + Crotamiton)/Diclofenac sodium | — | — | 12 | 40.0 | 25.0 | 44.0 | 1.5 | 1.7 | — | — | — | — |
| Crotamiton/Diclofenac sodium | — | — | 10 | 2.0 | 5.0 | 4.0 | 1.0 | 0.7 | — | — | — | — |
| Solubility | x | x | x | x | x | x | x | x | ○ | ○ | ○ | ○ |

○: Completely dissolved
x: Undissolved

Example 1

Diclofenac sodium (10.0 g) and purified water (10.0 g) were added to crotamiton (20.0 g), and then homogeneously stirred and dissolved to prepare a diclofenac sodium-principal drug solution of the present invention (corresponding to Example 1S). Kaolin (30 g) was added to 70% D-sorbitol solution (150 g), and then stirred and dispersed to prepare a mixture A. Furthermore, concentrated glycerin (250 g), carmellose sodium (40 g), partially neutralized polyacrylic acid (50 g), hydroxypropylcellulose (20.0 g), and dihydroxyaluminum aminoacetate (0.6 g) were mixed, and then stirred and dispersed to prepare a mixture B. The mixture A, 20% polyacrylic acid aqueous solution (200.0 g), the diclofenac sodium-principal drug solution of the present invention, disodium edetate (0.8 g), purified water (191.6 g), and the mixture B were sequentially added and kneaded to obtain a homogeneous gel. Additionally, polyvinyl alcohol (8.0 g) and tartaric acid (5.0 g) were homogeneously dispersed in said hydrous gel. Finally, l-menthol (2.5 g), methylparaben (1.0 g), and propylparaben (0.5 g) were dissolved in 1,3-butylene glycol (10.0 g), and then this solution was homogeneously dispersed in the above-prepared hydrous gel to obtain a plaster for a patch. This plaster was spread on a polyester non-woven fabric, and the plaster surface was coated with a polypropylene film to form an aqueous patch.

Example 2

Diclofenac sodium (10.0 g) and purified water (60.0 g) were added to crotamiton (20.0 g), and then homogeneously stirred and dissolved to prepare a diclofenac sodium-principal drug solution of the present invention (corresponding to Example 2S). Kaolin (30 g) and titanium oxide (5.0 g) were added to 70% D-sorbitol solution (150 g), and then stirred and dispersed to prepare a mixture A. Furthermore, concentrated glycerin (250.0 g), carmellose sodium (40.0 g), partially neutralized polyacrylic acid (50.0 g), hydroxypropylcellulose (20.0 g), and dihydroxyaluminum aminoacetate (0.6 g) were mixed, and then stirred and dispersed to prepare a mixture B. The mixture A, 20% polyacrylic acid aqueous solution (200.0 g), the diclofenac sodium-principal drug solution of the present invention, disodium edetate (0.8 g), purified water (136.6 g), and the mixture B were sequentially added and kneaded to obtain a homogeneous gel. Additionally, polyvinyl alcohol (8.0 g) and tartaric acid (5.0 g) were homogeneously dispersed in said hydrous gel. Finally, l-menthol (2.5 g), methylparaben (1.0 g), and propylparaben (0.5 g) were dissolved in 1,3-butylene glycol (10.0 g), and then this solution was homogeneously dispersed in the above-prepared hydrous gel to obtain a plaster for a patch. This plaster was spread on a polyester non-woven fabric, and the plaster surface was coated with a polypropylene film to form an aqueous patch.

Example 3

Diclofenac sodium (10.0 g) and purified water (20.0 g) were added to crotamiton (40.0 g), and then homogeneously stirred and dissolved to prepare a diclofenac sodium-principal drug solution of the present invention (corresponding to Example 3S). Kaolin (30.0 g) was added to 70% D-sorbitol solution (150.0 g), and then stirred and dispersed to prepare a mixture A.

Furthermore, concentrated glycerin (250.0 g), carmellose sodium (40.0 g), partially neutralized polyacrylic acid (50.0 g), hydroxypropylcellulose (30.0 g), and dihydroxyaluminum aminoacetate (0.6 g) were mixed, and then stirred and dispersed to prepare a mixture B. The mixture A, 20% polyacrylic acid aqueous solution (200.0 g), the diclofenac sodium-principal drug solution of the present invention, disodium edetate (0.8 g), purified water (151.6 g), and the mixture B were sequentially added and kneaded to obtain a homogeneous gel. Additionally, polyvinyl alcohol (8.0 g) and tartaric acid (5.0 g) were homogeneously dispersed in said hydrous gel. Finally, l-menthol (2.5 g) and methylparaben (1.5 g) were dissolved in 1,3-butylene glycol (10.0 g), and then this solution was homogeneously dispersed in the above-prepared hydrous gel to obtain a plaster for a patch. This plaster was spread on a polyester non-woven fabric, and the plaster surface was coated with polyester film to form an aqueous patch.

Example 4

Diclofenac sodium (10.0 g) and purified water (20.0 g) were added to crotamiton (20.0 g), and then homogeneously stirred and dissolved to prepare a diclofenac sodium-principal drug solution of the present invention (corresponding to Example 4S). Kaolin (30.0 g) was added to 70% D-sorbitol solution (150.0 g), and then stirred and dispersed to prepare a mixture A. Furthermore, concentrated glycerin (250.0 g), carmellose sodium (40.0 g), partially neutralized polyacrylic acid (50.0 g), hydroxypropylcellulose (20.0 g), and dihydroxyaluminum aminoacetate (0.4 g) were mixed, and then stirred and dispersed to prepare a mixture B. The mixture A, 20% polyacrylic acid aqueous solution (200.0 g), the diclofenac sodium-principal drug solution of the present invention, disodium edetate (0.4 g), purified water (182.2 g), and the mixture B were sequentially added and kneaded to obtain a homogeneous gel. Additionally, polyvinyl alcohol (8.0 g) and tartaric acid (5.0 g) were homogeneously dispersed in said hydrous gel. Finally, l-menthol (2.5 g), methylparaben (1.0 g), and propylparaben (0.5 g) were dissolved in 1,3-butylene glycol (10.0 g), and then this solution was homogeneously dispersed in the above-prepared hydrous gel to obtain a plaster for a patch. This plaster was spread on a polyester non-woven fabric, and the plaster surface was coated with a polypropylene film to form an aqueous patch.

Comparative Example 1

According to the same process for preparation as that of the diclofenac sodium-principal drug solution in Example 1 (Example 1S) except that the purified water (10.0 g) was not added, a diclofenac sodium-principal drug solution in which diclofenac sodium was undissolved and dispersed (corresponding to Comparative Example 1S) was prepared. The subsequent process for preparation was the same as that of Example 1 and thus a plaster for a patch was obtained. This plaster was spread on a polyester non-woven fabric, and the plaster surface was coated with polyester film to form an aqueous patch.

Comparative Example 2

According to the same process for preparation as that of the diclofenac sodium-principal drug solution in Example 1 (Example 1S) except that purified water (20.0 g) was added in place of crotamiton (20.0 g), a diclofenac sodium-principal drug solution in which diclofenac sodium was undissolved and dispersed (corresponding to Comparative Example 2S) was prepared. The subsequent process for preparation was the same as that of Example 1 and thus a plaster for a patch was obtained. This plaster was spread on a polyester non-woven fabric, and the plaster surface was coated with a polypropylene film to form an aqueous patch.

Comparative Example 9

Diclofenac sodium (10.0 g) was added to propylene glycol (30.0 g), and then homogeneously stirred and dissolved to prepare a diclofenac sodium-principal drug solution (corresponding to Comparative Example 9S). Concentrated glycerin (180.0 g), carmellose sodium (40.0 g), partially neutralized polyacrylic acid (20.0 g), sodium polyacrylate (20.0 g), magnesium aluminometasilicate (1.5 g), and dried aluminum hydroxide gel (0.2 g) were mixed, and then stirred and dispersed to prepare a mixture A. The mixture A, 70% D-sorbitol solution (250.0 g), the diclofenac sodium-principal drug solution, disodium edetate (0.5 g), and purified water (390.8 g) were sequentially added and kneaded to obtain a homogeneous gel. Additionally, polyvinyl alcohol (40.0 g) and tartaric acid (3.0 g) were homogeneously dispersed in said hydrous gel. Finally, 1-menthol (2.5 g), methylparaben (1.0 g), and propylparaben (0.5 g) were dissolved in 1,3-butylene glycol (10.0 g), and then this solution was homogeneously dispersed in the above-prepared hydrous gel to obtain a plaster for a patch. This plaster was spread on a polyester non-woven fabric, and the plaster surface was coated with polyester film to form an aqueous patch.

Comparative Example 10

Diclofenac sodium (10.0 g), diisopropyl adipate (10.0 g), and crotamiton (5.0 g) were added to lauromacrogol (20.0 g), and then homogeneously stirred and dissolved to prepare a diclofenac sodium-principal drug solution (corresponding to Comparative Example 10S). Concentrated glycerin (250.0 g), carmellose sodium (40.0 g), sodium polyacrylate (60.0 g), hydroxypropylcellulose (5.0 g), and dihydroxyaluminum aminoacetate (1.2 g) were mixed, and then stirred and dispersed to prepare a mixture A. The mixture A, 1-menthol (2.5 g), methylparaben (1.0 g), propylparaben (0.5 g), 20% polyacrylic acid aqueous solution (80.0 g), diisopropanolamine (10.0 g), 70% D-sorbitol solution (180.0 g), the diclofenac sodium-principal drug solution, disodium edetate (0.8 g), and purified water (308.0 g) were sequentially added and kneaded to obtain a homogeneous gel. Additionally, polyvinyl alcohol (13.0 g) and tartaric acid (3.0 g) were homogeneously dispersed in said hydrous gel to obtain a plaster for a patch. This plaster was spread on a polyester non-woven fabric, and the plaster surface was coated with a polyester film to form an aqueous patch.

Comparative Example 11

Diclofenac sodium (10.0 g) was added to N-methyl-2-pyrrolidone (20.0 g), and then homogeneously stirred and dissolved to prepare a diclofenac sodium-principal drug solution (corresponding to Comparative Example 11S). Concentrated glycerin (180.0 g), carmellose sodium (40.0 g), partially neutralized polyacrylic acid (20.0 g), sodium polyacrylate (20.0 g), magnesium aluminometasilicate (1.5 g), and dried aluminum hydroxide gel (0.2 g) were mixed, and then stirred and dispersed to prepare a mixture A. The mixture A, 70% D-sorbitol solution (250.0 g), the diclofenac sodium-principal drug solution, disodium edetate (0.5 g), and purified water (400.8 g) were sequentially added and kneaded to obtain a homogeneous gel. Additionally, polyvinyl alcohol (40.0 g) and tartaric acid (3.0 g) were homogeneously dispersed in said hydrous gel. Finally, 1-menthol (2.5 g) and methylparaben (1.5 g) were dissolved in 1,3-butylene glycol (10.0 g), and then this solution was homogeneously dispersed in the above-prepared hydrous gel to obtain a plaster for a patch. This plaster was spread on a polyester non-woven fabric, and the plaster surface was coated with a polyester film to form an aqueous patch.

Comparative Example 12

Oleic acid (20.0 g) and crotamiton (20.0 g) were added to diclofenac sodium (10.0 g), and then homogeneously stirred and dissolved to prepare a diclofenac sodium-principal drug solution (corresponding to Comparative Example 12S). Kaolin (30.0 g) was added to 70% D-sorbitol solution (150.0 g), and then stirred and dispersed to prepare a mixture A. Furthermore, concentrated glycerin (250.0 g), carmellose sodium (40.0 g), partially neutralized polyacrylic acid (50.0 g), hydroxypropylcellulose (20.0 g), and dihydroxyaluminum aminoacetate (0.4 g) were mixed, and then stirred and dispersed to prepare a mixture B. The mixture A, 20% polyacrylic acid aqueous solution (200.0 g), the diclofenac sodium-principal drug solution, disodium edetate (0.4 g), purified water (182.2 g), and the mixture B were sequentially added and kneaded to obtain a homogeneous gel. Additionally, polyvinyl alcohol (8.0 g) and tartaric acid (5.0 g) were homogeneously dispersed in said hydrous gel. Finally, 1-menthol (2.5 g), methylparaben (1.0 g), and propylparaben (0.5 g) were dissolved in 1,3-butylene glycol (10.0 g), and then this solution was homogeneously dispersed in the above-prepared hydrous gel to obtain a plaster for a patch. This plaster was spread on a polyester non-woven fabric, and the plaster surface was coated with a polypropylene film to form an aqueous patch.

Lists of prescriptions of Examples and Comparative Examples are shown in Table 2 and Table 3 respectively.

TABLE 2

List of prescriptions (Examples)

| Ingredient (% by weight) | Example 1 | Example 2 | Example 3 | Example 4 |
| --- | --- | --- | --- | --- |
| Diclofenac sodium | 1.0 | 1.0 | 1.0 | 1.0 |
| Crotamiton | 2.0 | 2.0 | 4.0 | 2.0 |
| Purified water (for diclofenac sodium-principal drug solution) | 1.0 | 6.0 | 2.0 | 2.0 |
| 1-Menthol | 0.25 | 0.25 | 0.25 | 0.25 |
| 1,3-Butylene glycol | 1.0 | 1.0 | 1.0 | 1.0 |
| Kaolin | 3.0 | 3.0 | 3.0 | 3.0 |
| Titanium oxide | — | 0.5 | — | — |
| Polyvinyl alcohol | 0.8 | 0.8 | 0.8 | 0.8 |
| Hydroxypropylcellulose | 2.0 | 2.0 | 3.0 | 2.0 |

TABLE 2-continued

List of prescriptions (Examples)

| Ingredient (% by weight) | Example 1 | Example 2 | Example 3 | Example 4 |
|---|---|---|---|---|
| D-Sorbitol solution | 15.0 | 15.0 | 15.0 | 15.0 |
| Concentrated glycerin | 25.0 | 25.0 | 25.0 | 25.0 |
| Carmellose sodium | 4.0 | 4.0 | 4.0 | 4.0 |
| Partially neutralized polyacrylic acid | 5.0 | 5.0 | 5.0 | 5.0 |
| 20% polyacrylic acid aqueous solution | 20.0 | 20.0 | 20.0 | 20.0 |
| Tartaric acid | 0.5 | 0.5 | 0.5 | 0.5 |
| Methylparaben | 0.1 | 0.1 | 0.15 | 0.1 |
| Dihydroxyaluminum aminoacetate | 0.06 | 0.06 | 0.06 | 0.04 |
| Propylparaben | 0.05 | 0.05 | — | 0.05 |
| Disodium edetate | 0.08 | 0.08 | 0.08 | 0.04 |
| Purified water (for dissolving ingredients of plaster) | 19.16 | 13.66 | 15.16 | 18.22 |
| Support | Polyester non-woven fabric 110 g/m$^2$ | Polyester non-woven fabric 110 g/m$^2$ | Polyester non-woven fabric 110 g/m$^2$ | Polyester non-woven fabric 110 g/m$^2$ |
| Liner | Polypropylene film | Polypropylene film | Polyester film | Polypropylene film |

TABLE 3

List of prescriptions (Comparative Examples)

| Ingredient (% by weight) | Com. 1 | Com. 2 | Com. 9 | Com. 10 | Com. 11 | Com. 12 |
|---|---|---|---|---|---|---|
| Diclofenac sodium | 1.0 | 1.0 | 1.0 | 1.0 | 1.0 | 1.0 |
| Crotamiton | 2.0 | — | — | 0.5 | — | 2.0 |
| Purified water | — | 3.0 | — | — | — | — |
| Propylene glycol | — | — | 3.0 | — | — | — |
| N-Methyl-2-pyrrolidone | — | — | — | — | 2.0 | — |
| Lauromacrogol (Polyoxyethylene laurylether) | — | — | — | 2.0 | — | — |
| Diisopropyl adipate | — | — | — | 1.0 | — | — |
| Oleic acid | — | — | — | — | — | 2.0 |
| 1-Menthol | 0.25 | 0.25 | 0.25 | 0.25 | 0.25 | 0.25 |
| 1,3-Butylene glycol | 1.0 | 1.0 | 1.0 | — | 1.0 | 1.0 |
| Kaolin | 3.0 | 3.0 | — | — | — | 3.0 |
| Polyvinyl alcohol | 0.8 | 0.8 | 4.0 | 1.3 | 4.0 | 0.8 |
| Hydroxypropylcellulose | 2.0 | 2.0 | — | 0.5 | — | 2.0 |
| Dried aluminum hydroxide gel | — | — | 0.02 | — | 0.02 | — |
| Sodium polyacrylate | — | — | 2.0 | 6.0 | 2.0 | — |
| Diisopropanolamine | — | — | — | 1.0 | — | — |
| 20% polyacrylic acid aqueous solution | 20.0 | 20.0 | — | 8.0 | — | 20.0 |
| D-Sorbitol solution | 15.0 | 15.0 | 25.0 | 18.0 | 25.0 | 15.0 |
| Concentrated glycerin | 25.0 | 25.0 | 18.0 | 25.0 | 18.0 | 25.0 |
| Carmellose sodium | 4.0 | 4.0 | 4.0 | 4.0 | 4.0 | 4.0 |
| Partially neutralized polyacrylic acid | 5.0 | 5.0 | 2.0 | — | 2.0 | 5.0 |
| Tartaric acid | 0.5 | 0.5 | 0.3 | 0.3 | 0.3 | 0.5 |
| Methylparaben | 0.1 | 0.1 | 0.1 | 0.1 | 0.15 | 0.1 |
| Magnesium aluminometasilicate | — | — | 0.15 | — | 0.15 | — |
| Dihydroxyaluminum aminoacetate | 0.06 | 0.06 | — | 0.12 | — | 0.04 |
| Propylparaben | 0.05 | 0.05 | 0.05 | 0.05 | — | 0.05 |
| Disodium edetate | 0.08 | 0.08 | 0.05 | 0.08 | 0.05 | 0.04 |
| Purified water (for dissolving ingredients of plaster) | 20.16 | 19.16 | 39.08 | 30.8 | 40.08 | 18.22 |
| Support | Polyester non-woven fabric 110 g/m$^2$ | Polyester non-woven fabric 100 g/m$^2$ | Polyester non-woven fabric 125 g/m$^2$ | Polyester non-woven fabric 115 g/m$^2$ | Polyester non-woven fabric 125 g/m$^2$ | Polyester non-woven fabric 110 g/m$^2$ |
| Liner | Polyester film | Polypropylene film | Polyester film | Polyester film | Polyester film | Polypropylene film |

Experimental Example 2

<Observation About Whether Crystal Precipitation of Diclofenac Sodium is Found or Not in Plaster>

Using each patch of Examples 1-4, Comparative Examples 1-2, 9-11 and 12, an observation was made by a polarizing microscope about whether a crystal precipitation of diclofenac sodium was found or not in a plaster after the each patch had been left at 20° C. for 24 hours and at 40° C. for 2 months. The results are shown in Table 4.

TABLE 4

Observation about whether a crystal precipitation of diclofenac sodium was found (Yes) or not (No)

| Storage time | Ex. 1 | Ex. 2 | Ex. 3 | Ex. 4 |
| --- | --- | --- | --- | --- |
| 20° C.-24 hr | No | No | No | No |
| 40° C.-2 M | No | No | No | No |

| Storage time | Com. 1 | Com. 2 | Com. 9 | Com. 10 | Com. 11 | Com. 12 |
| --- | --- | --- | --- | --- | --- | --- |
| 20° C.-24 hr | Yes | Yes | Yes | Yes | Yes | No |
| 40° C.-2 M | Yes | Yes | Yes | No | Yes | No |

Experimental Example 3

<Rat Skin Permeability Test of the Drug>

The skin permeability of diclofenac sodium about the each patch of Examples 1-4, Comparative Examples 1-2, 9-11 and 12 was assessed by using a hairless rat skin. A skin of a back of a hairless rat was peeled, the dermal side of the skin was fit as the receptor side on a Franz diffusion cell (1.77 cm$^2$, 10 mL), and warm water at 37° C. was circulated in the circumference of the cell. A formulation was stuck to the stratum corneum side of the skin, the receptor was filled with phosphate buffer solution (PBS) pH 7.4, and the sampling of the receptor solution was chronologically performed. Using the receptor solution which was taken as a sample per each time, the amount of diclofenac sodium which permeated the skin was determined by the high-performance liquid chromatographic method. The skin permeability rate per unit time and unit area was calculated from the obtained data. The results about Examples 1-4, Comparative Examples 1-2, 9-11 and 12 after 2 hours and 24 hours are shown in Table 5.

Furthermore, with respect to the each patch of Example 3 and Comparative Examples 9-11, the relation between the skin permeability rate of diclofenac sodium which permeated the hairless rat skin and time is shown in FIG. 1.

TABLE 5

Skin permeability rate (μg/cm$^2$/h, average, n = 4)

| Storage time | Ex. 1 | Ex. 2 | Ex. 3 | Ex. 4 |
| --- | --- | --- | --- | --- |
| 2 hours | 0.22 | 0.20 | 0.15 | 0.16 |
| 24 hours | 0.78 | 0.94 | 0.70 | 0.97 |

| Storage time | Com. 1 | Com. 2 | Com. 9 | Com. 10 | Com. 11 | Com. 12 |
| --- | --- | --- | --- | --- | --- | --- |
| 2 hours | 0.12 | 0.06 | 0.02 | 0.27 | 0.03 | 0.05 |
| 24 hours | 0.65 | 0.20 | 0.29 | 0.88 | 0.33 | 0.50 |

Experimental Example 4

<Drug Stability in Fog Formulation>

The each aqueous patch containing diclofenac sodium obtained from Examples 1-4, Comparative Examples 1-2, 9-11 and 12 was placed in a light-blocking airtight container, and incubated at 40° C. for 1 month and 2 months. The patch was taken out from the container on the each measurement date, and subjected to a methanol extraction with heating under reflux. After sufficiently cooled, the extract was measured by the liquid chromatography method, and the concentration of diclofenac sodium in the formulation was determined. The results are shown in Table 6.

TABLE 6

Remaining amount of the drug (%, average, n = 3)

| Storage time | Ex. 1 | Ex. 2 | Ex. 3 | Ex. 4 |
| --- | --- | --- | --- | --- |
| 40° C.-1 M | — | 96.9 | — | 98.5 |
| 40° C.-2 M | 94.2 | 94.4 | 97.1 | — |

| Storage time | Com. 1 | Com. 2 | Com. 9 | Com. 10 | Com. 11 | Com. 12 |
| --- | --- | --- | --- | --- | --- | --- |
| 40° C.-1 M | — | — | — | 92.4 | — | 96.9 |
| 40° C.-2 M | 92.8 | 102.7 | 101.6 | 87.9 | 102.3 | 92.8 |

The above experimental results show that the patches of Examples 1-4 were excellent in both of the formulation stability and the skin permeability of the drug. On the other hand, in the storage test after the preparation, the each patch of Comparative Examples 1-2 and 9-11 was observed to result in a crystal precipitation in the formulation. Especially, if the result of Experimental Example 6 is also taken into consideration, the patch of Comparative Example 10 resulted in not only a crystal precipitation, but also a lowered stability of the drug diclofenac sodium itself. Furthermore, the each patch of Comparative Examples 1-2, 9, 11 and 12 was also found to be inferior in the skin permeability of the drug as compared with the each patch of Examples.

Industrial Applicability

According to the present invention, an aqueous patch which is excellent in the dissolution stability and the transdermal absorbability of diclofenac sodium can be provided.

The invention claimed is:

1. An aqueous patch containing diclofenac sodium, wherein the patch contains a homogeneous mixed solution of diclofenac sodium in a plaster, wherein the solution is obtained by mixing crotamiton, diclofenac sodium and water in the mixture ratio of crotamiton/diclofenac sodium of 8.0 or less and the mixture ratio of (water+crotamiton)/diclofenac sodium of 3.0-20.0.

2. An aqueous patch containing diclofenac sodium in which 5% or less of diclofenac sodium and 5% or less of crotamiton per plaster weight are contained, wherein the patch contains a homogeneous mixed solution of diclofenac sodium in a plaster, wherein the solution is obtained by mixing crotamiton, diclofenac sodium and water in the mixture ratio of crotamiton/diclofenac sodium of 8.0 or less and the mixture ratio of (water+crotamiton)/diclofenac sodium of 3.0-20.0.

3. The aqueous patch containing diclofenac sodium according to claim 1, wherein the amount of crotamiton per plaster weight is 1.5-5%.

4. A process for preparing an aqueous patch containing diclofenac sodium characterized in that the process comprises mixing crotamiton, diclofenac sodium and water in the mixture ratio of crotamiton/diclofenac sodium of 8.0 or less and the mixture ratio of (water+crotamiton)/diclofenac sodium of 3.0-20.0 to obtain a homogeneous mixed solution of diclofenac sodium, followed by adding other ingredients of a plaster to this solution by a conventional method, and then spreading the obtained plaster composition (plaster) on a support.

5. A process for preparing an aqueous patch containing diclofenac sodium characterized in that the process comprises mixing crotamiton, diclofenac sodium and water in the mixture ratio of crotamiton/diclofenac sodium of 8.0 or less and the mixture ratio of (water+crotamiton)/diclofenac sodium of 3.0-20.0 to obtain a homogeneous mixed solution of diclofenac sodium, followed by adding other ingredients of a plaster to this solution by a conventional method to obtain a plaster composition containing 5% or less of diclofenac sodium and 5% or less of crotamiton per plaster weight, and then spreading the composition on a support.

6. The aqueous patch containing diclofenac sodium according to claim 2, wherein the amount of crotamiton per plaster weight is 1.5-5%.

* * * * *